United States Patent
Yu et al.

(10) Patent No.: US 9,878,163 B2
(45) Date of Patent: *Jan. 30, 2018

(54) SYSTEM AND METHOD FOR ASSESSING AND SELECTING STIMULATION VECTORS IN AN IMPLANTABLE CARDIAC RESYNHRONIZATION THERAPY DEVICE

(71) Applicant: Cardiac Pacemakers, Inc., St. Paul, MN (US)

(72) Inventors: Yinghong Yu, Shoreview, MN (US); Keith L. Herrmann, Minneapolis, MN (US); Holly Rockweiler, San Francisco, CA (US); Sunipa Saha, Shoreview, MN (US); Benjamin J Nyquist, Apple Valley, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/276,860

(22) Filed: Sep. 27, 2016

(65) Prior Publication Data
US 2017/0014631 A1   Jan. 19, 2017

Related U.S. Application Data

(63) Continuation of application No. 14/574,787, filed on Dec. 18, 2014, now Pat. No. 9,457,191.

(Continued)

(51) Int. Cl.
*A61N 1/368* (2006.01)
*A61N 1/372* (2006.01)
*G06F 19/00* (2011.01)

(52) U.S. Cl.
CPC ......... *A61N 1/3686* (2013.01); *A61N 1/3684* (2013.01); *A61N 1/37247* (2013.01); *G06F 19/3406* (2013.01); *G06F 19/3481* (2013.01)

(58) Field of Classification Search
None
See application file for complete search history.

(56) References Cited

U.S. PATENT DOCUMENTS 6,128,535 A   10/2000   Maarse
6,192,275 B1   2/2001   Zhu et al.
(Continued)

FOREIGN PATENT DOCUMENTS

CN   105848711 A   8/2016
WO   WO-2015095593 A1   6/2015

OTHER PUBLICATIONS

"U.S. Appl. No. 14/574,787, Non Final Office Action dated Feb. 18, 2016", 8 pgs.

(Continued)

*Primary Examiner* — Kennedy Schaetzle
(74) *Attorney, Agent, or Firm* — Schwegman Lundberg & Woessner, P.A.

(57) ABSTRACT

Systems and methods for providing CRT therapy to a patient with an implanted multi-site pacing medical device. In one example, an intrinsic electrical delay associated with each of two or more left ventricle electrodes may be determined. The intrinsic electrical delay associated with each of the two or more left ventricle electrodes may be compared to an electrical delay threshold. If the electrical delay associated with one or fewer left ventricle electrodes is greater than the electrical delay threshold, a single left ventricle electrode may be selected for use during subsequent CRT therapy. If the electrical delay associated with more than one left ventricle electrode is greater than the electrical delay threshold, two or more of the left ventricle electrodes may be selected for use during subsequent CRT therapy.

20 Claims, 5 Drawing Sheets

Related U.S. Application Data

(60) Provisional application No. 61/917,833, filed on Dec. 18, 2013.

(56) References Cited

U.S. PATENT DOCUMENTS

| | | | |
|---|---|---|---|
| 6,226,551 B1 | 5/2001 | Zhu et al. |
| 6,421,564 B1 | 7/2002 | Yerich et al. |
| 6,463,327 B1 | 10/2002 | Lurie et al. |
| 6,493,586 B1 | 12/2002 | Stahmann et al. |
| 6,587,726 B2 | 7/2003 | Lurie et al. |
| 6,615,089 B1 | 9/2003 | Russie et al. |
| 6,772,008 B2 | 8/2004 | Zhu et al. |
| 6,922,589 B2 | 7/2005 | Stahmann et al. |
| 6,937,901 B2 | 8/2005 | Zhu et al. |
| 6,978,178 B2 | 12/2005 | Sommer et al. |
| 7,031,773 B1 | 4/2006 | Levine et al. |
| 7,123,963 B2 | 10/2006 | Sawchuk |
| 7,200,439 B2 | 4/2007 | Zdeblick et al. |
| 7,225,016 B1 | 5/2007 | Koh |
| 7,225,035 B2 | 5/2007 | Brabec et al. |
| 7,228,174 B2 | 6/2007 | Burnes et al. |
| 7,277,757 B2 | 10/2007 | Casavant et al. |
| 7,299,093 B2 | 11/2007 | Zhu et al. |
| 7,328,067 B2 | 2/2008 | Zhu et al. |
| 7,340,302 B1 | 3/2008 | Falkenberg et al. |
| 7,363,086 B1 | 4/2008 | Koh et al. |
| 7,392,086 B2 | 6/2008 | Sathaye |
| 7,412,287 B2 | 8/2008 | Yonce et al. |
| 7,469,161 B1 | 12/2008 | Gandhi et al. |
| 7,471,983 B2 | 12/2008 | Voegele et al. |
| 7,496,409 B2 | 2/2009 | Greenhut et al. |
| 7,509,170 B2 | 3/2009 | Zhang et al. |
| 7,555,336 B2 | 6/2009 | Sheth et al. |
| 7,555,340 B2 | 6/2009 | Dong et al. |
| 7,587,240 B2 | 9/2009 | Zhang et al. |
| 7,620,452 B1 | 11/2009 | Russie |
| 7,657,314 B2 | 2/2010 | Sathaye et al. |
| 7,680,536 B2 | 3/2010 | Sathaye et al. |
| 7,711,423 B2 | 5/2010 | Burnes et al. |
| 7,734,333 B2 | 6/2010 | Ghanem et al. |
| 7,738,959 B2 | 6/2010 | Manrodt et al. |
| 7,761,164 B2 | 7/2010 | Verhoef et al. |
| 7,792,585 B1 | 9/2010 | Shelchuk |
| 7,848,812 B2 | 12/2010 | Crowley et al. |
| 7,953,489 B2 | 5/2011 | Warren et al. |
| 7,957,803 B2 | 6/2011 | Zhang et al. |
| 7,996,072 B2 | 8/2011 | Haefner et al. |
| 8,010,203 B2 | 8/2011 | Demulling et al. |
| 8,014,860 B2 | 9/2011 | Kwok et al. |
| 8,036,743 B2 | 10/2011 | Savage et al. |
| 8,065,002 B2 | 11/2011 | Arand et al. |
| 8,078,276 B2 | 12/2011 | Dong et al. |
| 8,135,463 B2 | 3/2012 | Burnes et al. |
| 8,145,311 B2 | 3/2012 | Min |
| 8,150,512 B2 | 4/2012 | Bornzin et al. |
| 8,160,700 B1 | 4/2012 | Ryu et al. |
| 8,175,703 B2 | 5/2012 | Dong et al. |
| 8,185,202 B2 | 5/2012 | Sathaye |
| 8,200,331 B2 | 6/2012 | Libbus et al. |
| 8,200,332 B2 | 6/2012 | Libbus et al. |
| 8,209,010 B2 | 6/2012 | Ryu et al. |
| 8,209,013 B2 | 6/2012 | Brooke et al. |
| 8,233,979 B1 | 7/2012 | Shelchuk |
| 8,255,048 B2 | 8/2012 | Dal Molin et al. |
| 8,260,421 B2 | 9/2012 | Sathaye |
| 8,265,736 B2 | 9/2012 | Sathaye et al. |
| 8,265,755 B2 | 9/2012 | Min |
| 8,265,759 B2 | 9/2012 | Tehrani et al. |
| 8,271,086 B2 | 9/2012 | Voegele et al. |
| 8,271,087 B2 | 9/2012 | Sathaye et al. |
| 8,285,377 B2 | 10/2012 | Rosenberg et al. |
| 8,301,246 B2 | 10/2012 | Park et al. |
| 8,306,622 B2 | 11/2012 | Arcot-Krishnamurthy et al. |
| 8,326,418 B2 | 12/2012 | Sommer et al. |
| 8,326,419 B2 | 12/2012 | Rosenberg et al. |
| 8,335,565 B2 | 12/2012 | Freeberg et al. |
| 8,346,372 B2 | 1/2013 | Yang et al. |
| 8,401,646 B2 | 3/2013 | Stadler et al. |
| 8,447,400 B2 | 5/2013 | More et al. |
| 8,744,572 B1 | 6/2014 | Greenhut et al. |
| 8,838,237 B1 | 9/2014 | Niazi |
| 9,457,191 B2 * | 10/2016 | Yu .................. A61N 1/37247 |
| 2002/0178191 A1 | 11/2002 | Sielken |
| 2005/0090870 A1 | 4/2005 | Hine et al. |
| 2006/0155202 A1 | 7/2006 | Arand et al. |
| 2007/0129764 A1 | 6/2007 | Burnes |
| 2008/0077186 A1 | 3/2008 | Thompson et al. |
| 2009/0043351 A1 | 2/2009 | Sathaye et al. |
| 2009/0043352 A1 | 2/2009 | Brooke et al. |
| 2009/0054946 A1 | 2/2009 | Sommer et al. |
| 2009/0210024 A1 | 8/2009 | Brooke |
| 2010/0125306 A1 | 5/2010 | McCabe et al. |
| 2010/0152801 A1 | 6/2010 | Koh et al. |
| 2010/0198292 A1 | 8/2010 | Honeck et al. |
| 2010/0305637 A1 | 12/2010 | McCabe et al. |
| 2010/0305638 A1 | 12/2010 | McCabe et al. |
| 2010/0305647 A1 | 12/2010 | Mccabe et al. |
| 2010/0324617 A1 | 12/2010 | Ong |
| 2011/0004264 A1 | 1/2011 | Siejko et al. |
| 2011/0022110 A1 | 1/2011 | Min |
| 2011/0022112 A1 | 1/2011 | Min |
| 2011/0098770 A1 | 4/2011 | Ryu et al. |
| 2011/0098773 A1 | 4/2011 | Brisben et al. |
| 2011/0098774 A1 | 4/2011 | Brisben et al. |
| 2011/0106213 A1 | 5/2011 | Davis et al. |
| 2011/0152956 A1 | 6/2011 | Hincapie Ordonez et al. |
| 2011/0196441 A1 | 8/2011 | Ryu et al. |
| 2011/0196442 A1 | 8/2011 | Ryu et al. |
| 2011/0245890 A1 | 10/2011 | Brisben et al. |
| 2011/0319954 A1 | 12/2011 | Niazi et al. |
| 2012/0035685 A1 | 2/2012 | Saha et al. |
| 2012/0078320 A1 | 3/2012 | Schotzko et al. |
| 2012/0101543 A1 | 4/2012 | Demmer et al. |
| 2012/0101546 A1 | 4/2012 | Stadler et al. |
| 2012/0130442 A1 | 5/2012 | Rockweiler et al. |
| 2012/0150253 A1 | 6/2012 | Burnes et al. |
| 2012/0185012 A1 | 7/2012 | Ryu et al. |
| 2012/0185013 A1 | 7/2012 | Sivard et al. |
| 2012/0191154 A1 | 7/2012 | Ryu et al. |
| 2012/0229496 A1 | 9/2012 | Bloemer |
| 2012/0253359 A1 | 10/2012 | Koh et al. |
| 2012/0271371 A1 | 10/2012 | Keel et al. |
| 2012/0290036 A1 | 11/2012 | Karamanoglu et al. |
| 2012/0296387 A1 | 11/2012 | Zhang et al. |
| 2012/0296388 A1 | 11/2012 | Zhang et al. |
| 2012/0323291 A1 | 12/2012 | Sathaye et al. |
| 2012/0330372 A1 | 12/2012 | Sathaye et al. |
| 2013/0006332 A1 | 1/2013 | Sommer et al. |
| 2013/0030487 A1 | 1/2013 | Keel et al. |
| 2013/0035737 A1 | 2/2013 | Ryu et al. |
| 2013/0035738 A1 | 2/2013 | Karst et al. |
| 2013/0046356 A1 | 2/2013 | Jensen et al. |
| 2013/0046369 A1 | 2/2013 | Eggen et al. |
| 2013/0053916 A1 | 2/2013 | Sambelashvili et al. |
| 2013/0053918 A1 | 2/2013 | Sambelashvili et al. |
| 2013/0183182 A1 | 7/2013 | White, Jr. |
| 2013/0261687 A1 | 10/2013 | Xi et al. |
| 2015/0134023 A1 | 5/2015 | Mcspadden et al. |
| 2015/0165204 A1 | 6/2015 | Yu et al. |

OTHER PUBLICATIONS

"U.S. Appl. No. 14/574,787, Notice of Allowance dated Jun. 6, 2016", 7 pgs.

"U.S. Appl. No. 14/574,787, Response filed May 5, 2016 to Non Final Office Action dated Feb. 18, 2016", 10 pgs.

"Family of digital implantable cardioverter defibrillators with cardiac resynchronization therapy", Medtronic, VIVATM I VIVATM QUAD, BRAVATM I BRAVATM QUAD CRT-D. Reference Manual, (2012), 418.

"International Application Serial No. PCT/US2014/071273, International Search Report dated Apr. 7, 2015", 7 pgs.

(56) References Cited

OTHER PUBLICATIONS

"International Application Serial No. PCT/US2014/071273, Written Opinion dated Apr. 7, 2015", 8 pgs.

"St. Jude Medical 2013 Investor Conference", Power Point Slideshow, (Feb. 1, 2013).

"St. Jude Medical, Inc. announced first enrollment of its MultiPoint", Business Wire, Press Release, St. Paul, Minnesota, (May 2, 2013).

Coyle, Mike, "Executive Vice President & Cardiac and Vascular group President Medtronic Inc.", Medtronic. Medtronic 2012 Investor Conference Power Point Slideshow New York City, (Jun. 1, 2012).

Ginks, M. R, et al., "Multi-site left ventricular pacing as a potential treatment for patients with postero-lateral scar: insights from cardiac magnetic resonance imaging and invasive haemodynamic assessment", Europace 14(3), 373-379.

LeClercq, C, et al., "A randomized comparison of triple-site versus dual-site ventricular stimulation in patients with congestive heart failure", J Am Coll Cardiol 51(15), (2008), 1455-1462.

Niazi, I, et al., "Hemodynamic superiority of dual-site left ventricular stimulation over conventional biventricular stimulation in heart failure patients", Journal of Innovations in Cardiac Rhythm Management 2(8), (2011), 412-418.

Pappone, C, et al., "Cardiac pacing in heart failure patients with left bundle branch block: impact of pacing site for optimizing left ventricular resynchronization", Ital Heart J 1(7), (2000), 464-469.

Rogers, D. P, et al., "A randomized double-blind crossover trial of triventricular versus biventricular pacing in heart failure", Eur J Heart Fail, 14(5), 495-505.

"European Application Serial No. 14830443.9, Response filed Apr. 10, 2017 to Communication Pursuant to Rules 161(1) and 162 EPC dated Sep. 29, 2016", 8 pgs.

"International Application Serial No. PCT/US2014/071273, International Preliminary Report on Patentability dated Jun. 30, 2016", 10 pgs.

\* cited by examiner

SYSTEM AND METHOD FOR ASSESSING AND SELECTING STIMULATION VECTORS IN AN IMPLANTABLE CARDIAC RESYNHRONIZATION THERAPY DEVICE

CROSS-REFERENCE TO RELATED APPLICATIONS

This application is a continuation of U.S. application Ser. No. 14/574,787, filed Dec. 18, 2014, now issued as U.S. Pat. No. 9,457,191, which claims priority under 35 U.S.C. §119 to U.S. Provisional Application Ser. No. 61/917,833, filed Dec. 18, 2013, each of which is incorporated herein by reference in its entirety.

TECHNICAL FIELD

The present disclosure generally relates to systems and methods for configuring an implantable medical device and, more specifically for assessing and selecting one or more vectors for delivery of electrical stimulation for a medical device with a plurality of electrodes.

BACKGROUND

Cardiac rhythm management devices can include implantable or ambulatory devices, such as pacemakers, cardioverter defibrillators, and/or devices that can monitor one or more physiological parameters, and/or provide one or a combination of pacing, defibrillation, or cardiac resynchronization therapies. Such devices can be configured for use with a plurality of implanted or external electrodes, such as to detect and/or treat cardiac conditions. These electrodes may be configured in a plurality of different combinations for sensing cardiac electrical activity and/or delivering electrical stimulation therapy. Using different combinations of electrodes for sensing cardiac electrical activity may result in differing results for different electrode combinations for sensed electrical activity of a same cardiac cycle. Using different combinations of electrodes for delivering electrical stimulation therapy to the heart may similarly result in differing effectiveness of the therapy. Each of these electrode configurations may be termed a "vector." Selecting a proper vector for sensing cardiac electrical activity and/or for delivering electrical stimulation therapy can help improve treatment.

SUMMARY

The present disclosure generally relates to systems and methods for assessing a plurality of vectors in an implantable medical device system implanted proximate a patient's heart and, more particularly to selecting one or more of the vectors, based on the assessment, for sensing cardiac electrical data and/or delivering electrical stimulation therapy. Selecting one or more vectors based on an assessment for sensing cardiac electrical data can help the implantable medical device system capture desired cardiac electrical data in a consistent manner. Such cardiac electrical data can be important for assisting the implantable medical device in determining proper timing and other parameters for delivering electrical stimulation therapy to a patient's heart. Selecting one or more vectors based on an assessment for delivering electrical stimulation therapy can help improve the effectiveness of the electrical stimulation therapy.

In one example, a method for providing CRT therapy to a patient with an implanted multi-site pacing medical device may include: determining an intrinsic electrical delay associated with each of two or more left ventricle electrodes, comparing the intrinsic electrical delay associated with each of the two or more left ventricle electrodes to an electrical delay threshold, if the electrical delay associated with one or fewer left ventricle electrodes is greater than the electrical delay threshold, selecting a left ventricle electrode for use during subsequent CRT therapy, and if the electrical delay associated with more than one left ventricle electrode is greater than the electrical delay threshold, selecting two or more of the left ventricle electrodes for use during subsequent CRT therapy.

In another example, a method of providing CRT therapy to a patient with an implanted multi-site pacing medical device may include: sensing an electrical delay between a pair of electrodes for each of a plurality of electrode pairs, comparing the sensed electrical delay of each of the plurality of electrode pairs to an electrical delay threshold, if the electrical delay of one or fewer electrode pairs is greater than the electrical delay threshold, selecting a single electrode to act as a cathode for subsequent CRT therapy, and if the electrical delay of more than one electrode pair is greater than the electrical delay threshold, selecting two or more electrodes to each act as a cathode during subsequent CRT therapy.

In another example, a medical device system for providing CRT therapy to a patient may include: a pulse generator, two or more left ventricle electrodes operatively coupled to the pulse generator, and a controller. The controller may be configured to: determine an intrinsic electrical delay associated with each of the two or more left ventricle electrodes, compare the intrinsic electrical delay associated with each of the two or more left ventricle electrodes to an electrical delay threshold, if the electrical delay associated with one or fewer left ventricle electrodes is greater than the electrical delay threshold, selecting a single left ventricle electrode for use during subsequent CRT therapy, and if the electrical delay associated with more than one left ventricle electrode is greater than the electrical delay threshold, selecting two or more of the left ventricle electrodes for use during subsequent CRT therapy.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
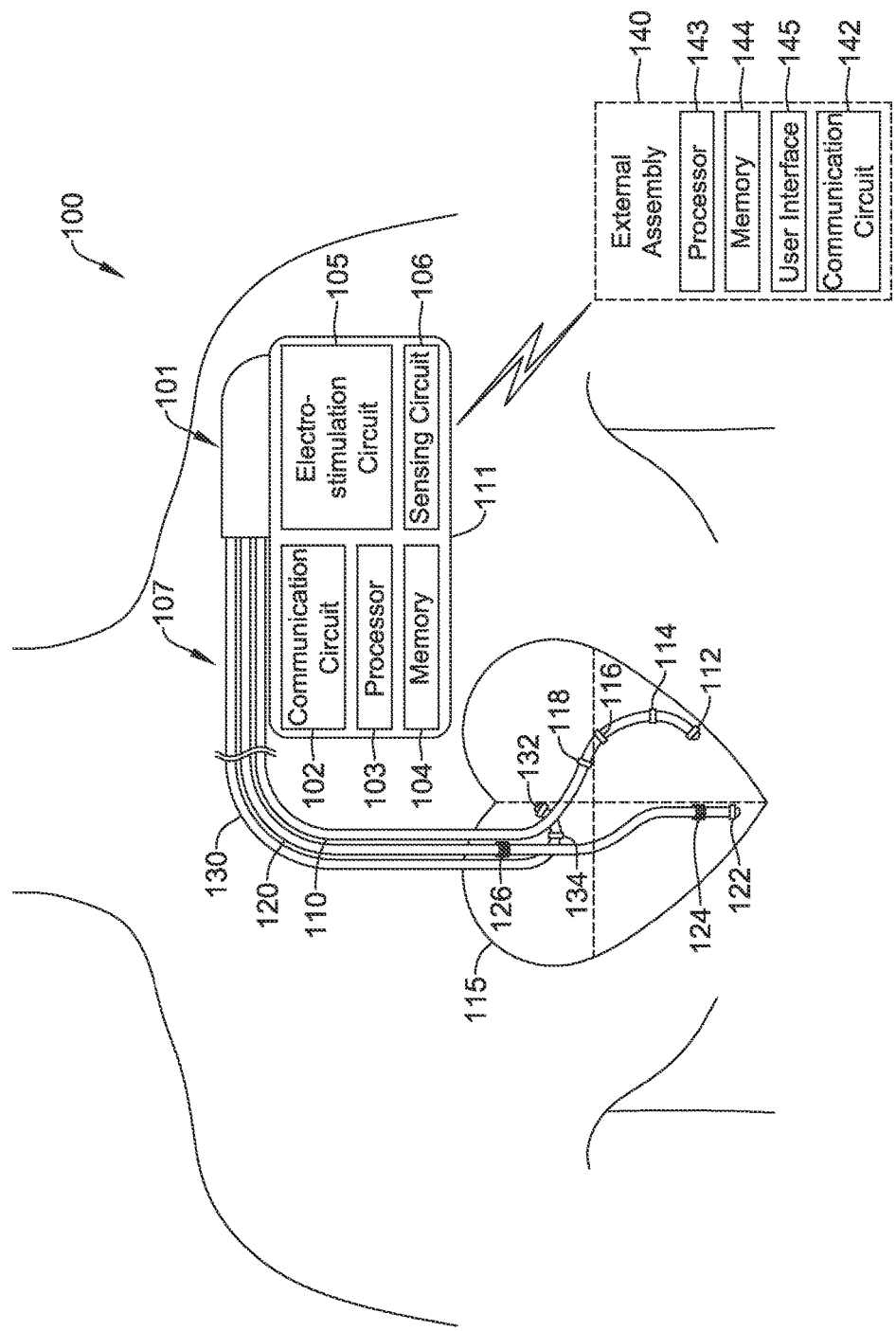
FIG. 1 is a schematic view of an implantable medical system that may be used in accordance with various embodiments described herein.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer conduct intrinsic electrical stimulation signals. In other examples, diseased tissue may not conduct the intrinsic signals as quickly as healthy tissue, thereby de-synchronizing the contraction of the heart. That is, portions of the heart muscle may contract earlier or later than other muscle cells of the heart due to the different conductivity of the heart tissue with respect to the intrinsic electrical signals. This un-coordinated contraction can result in a decrease in the flow of blood throughout the rest of the body, causing various health problems.

A number of implantable medical device (IMD) systems have been developed to assist such diseased hearts. These IMD systems may include electrodes implanted on or within the heart of the patient. The IMD systems may deliver electrical stimulation therapy to the heart through these electrodes. The delivered electrical stimulation therapy may replace or assist the intrinsically generated electrical signals in causing the contraction of the heart. One type of electrical stimulation therapy is termed cardiac resynchronization therapy (CRT). In general, CRT comprises delivering electrical stimulation pulses or therapy to a heart, sometimes referred to as "pacing," in order to assist all portions of the heart to contract in a normal, synchronous manner.

Some IMD systems for delivering CRT include multiple electrodes. However, these IMD systems may only use a subset of these electrodes for sensing cardiac electrical signals or for delivering electrical stimulation therapy. For example, some IMD systems may use a configuration of two electrodes in delivering electrical stimulation therapy, with one electrode acting as a cathode and one electrode acting as an anode. When delivering electrical stimulation to a heart via such an electrode pair, the path through the heart tissue taken by the electrical stimulation, e.g. its propagation pathway, may be termed a vector. Many physiological and physical factors affect which vectors in an IMD system implanted in a given heart will be suitable for delivering CRT to the heart. For example, a heart may have a region of diseased tissue which does not conduct electrical signals or conducts electrical signals more slowly than the surrounding tissue. In other examples, connections between the implanted electrodes and the heart tissue may cause variability in the power, effectiveness or propagation speed of delivered CRT. Accordingly, IMD systems with multiple available vectors, for example because the IMD system has three of more electrodes, may perform evaluations of all potential vectors before selecting which vector to use for delivering electrical stimulation therapy.

Some IMD systems may further deliver CRT via multiple vectors. For example, some IMD systems may use multiple cathode electrodes and a single anode electrode for delivering CRT. Delivering CRT via multiple vectors can, for example, help the delivered CRT capture a greater area of the heart by engaging multiple areas surrounding damaged tissue. Delivering CRT via multiple vectors can also help create a more synchronous contraction of the heart by having the delivered stimulation spread more rapidly throughout the heart. However, delivering CRT therapy via multiple vectors (e.g. "multi-site pacing") often uses more power than delivering CRT therapy via a single vector (e.g. "single-site pacing"). As many IMD systems are not easily accessible for battery replacement or recharging, prolonging battery life is often an important design consideration.

The present disclosure relates to systems and techniques for determining when to use single-site pacing or multi-site pacing in order to provide effective therapy. The present disclosure also relates to systems and techniques for delivering CRT in a multi-pacing configuration to produce efficient cardiac contractions.

FIG. 1 illustrates generally an example of a system 100 that can include an implantable medical device 101. Implantable medical device 101 can be coupled to one or more electrodes, which can be carried by one or more implantable leads, such as implantable leads 110, 120, and 130. Implantable leads 110, 120, and 130 can be configured to receive or sense cardiac electrical signals from heart 115. Implantable medical device 101 can include a hermetically-sealed or similar housing 111. Housing 111 can include titanium or another biocompatible material, such as one or more other conductive materials.

In one example, implantable medical device 101 can include one or more of a pacemaker, a defibrillator, an implantable monitor, a drug delivery device, a cardiac resynchronization therapy (CRT) device, a neural stimulation device, or one or more other implantable assemblies configured to monitor a person or configured to provide one or more treatments to the person. Examples of such monitoring or treatment can include delivering electrical stimulation therapy to tissues such as cardiac tissue, or electrical monitoring of muscular or cardiac activity. In one example, implantable medical device 101 can include an external medical device, such as a pacing system analyzer, programmer recorder monitor, or other external medical device that can be used to configure a system of multipolar implantable leads. In some cases, the implantable medical device 101 may include a subcutaneous Implantable Cardioverter-Defibrillator (S-ICD) and/or a subcutaneous pacemaker.

In some instances, the one or more of the electrodes may be provided by a leadless pacemaker (LCP), which is in communication with other LCP's and/or with another implantable medical device 101. The use of LCP may reduce or eliminate the need for one or more of the implantable leads 110, 120 and 130.

In the example of FIG. 1, implantable medical device 101 can be coupled to heart 115, or other body tissue, such as via electrode system 107, epicardial electrodes, or external (e.g., skin-patch) electrodes. In the system of FIG. 1, electrode system 107 includes at least one lead and at least one electrode for each lead. FIG. 1 shows an example in which there are three implantable leads 110, 120, and 130. In the example of FIG. 1, implantable lead 110 can be configured for use in association with a left ventricle of heart 115. For example, implantable lead 110 can be sized and shaped to allow insertion into a coronary sinus and intravascular advancement such as to put at least one electrode in association with the left ventricle of the heart 115. Implantable lead 110 can be a multipolar lead, including a plurality of electrodes and corresponding conductors. In an example, implantable lead 110 can include four discrete electrodes, such as: tip electrode 112, first ring electrode 114, second ring electrode 116, and third ring electrode 118. In an example, electrodes 114, 116, and 118 can be located near a distal portion of implantable lead 110. Each of electrodes 114, 116, and 118 can be separated by electrically insulating material, thus electrically isolating the individual electrodes. Each of the four left ventricular electrodes 112, 114, 116, and 118 can correspond to a unique electrical conductor and can be individually addressable by sensing circuit 106 or electro-stimulation circuit 105 contained within implantable medical device 101.

In the example of FIG. 1, implantable lead 120 can include tip electrode 122, first coil electrode 124, and second coil electrode 126. As generally shown in FIG. 1, implantable lead 120 can, in one example, be inserted into the right atrium and right ventricle of heart 115 so that first coil electrode 124 is positioned in the right ventricle and second coil electrode 126 is positioned in the right atrium.

In the example of FIG. 1, implantable lead 130 can include tip electrode 132 and ring electrode 134. As generally shown in FIG. 1, implantable lead 130 can be configured for insertion into the right atrium of heart 115.

The physical illustration of implantable leads 110, 120, and 130 provided in FIG. 1 is provided as an illustrative non-limiting example only. Other systems may include leads positioned differently with respect to a heart. Additionally, other systems may have differing numbers of electrodes and the positioning of the leads on the electrodes may differ. Other systems may also include more or less implantable leads. In a system that uses strictly LCPs, no leads may be required or even desired. In general, the systems and techniques of the present disclosure are amenable to any system including a plurality of electrodes that are configurable into a plurality of vectors, regardless of specific implant locations or electrode placement or numbers.

In one example, implantable medical device 101 can include a communication circuit 102, processor circuit 103, memory circuit 104, electro-stimulation circuit 105, and sensing circuit 106. Processor circuit 103 and memory circuit 104 can be used to control the operation of implantable medical device 101. For example, processor circuit 103 can be configured to detect a cardiac condition, such as by using the sensing circuit 106 or another physiological sensor, and to respond to the detected cardiac condition, such as by causing electro-stimulation circuit 105 to deliver electrical stimulation to heart 115 via one or more electrodes. Memory circuit 104 can include one or more parameters, such as for various pacing and sensing modes, test procedures or the like. Memory circuit 104 can be configured to store physiological data, such as data concerning the condition of heart 115. Memory circuit 104 can also be configured to store device data, such as data about a status of a test or a test result. In one example, implantable medical device 101 can use electro-stimulation circuit 105 or sensing circuit 106 to interface with electrode system 107. Electro-stimulation circuit 105 or sensing circuit 106 can be configured to generate an electro-stimulation signal to provide electrical stimulation therapy to heart 115, for example by using energy stored in a battery (not shown) that is stored within implantable medical device 101. Electro-stimulation circuit 105 or sensing circuit 106 can be electrically coupled to electrode system 107. For example, electrical stimulation can be transmitted from electro-stimulation circuit 105 to electrode system 107. Likewise, sensing circuit 106 may receive signals from electrode system 107. Communication circuit 102 can be configured to establish a data communication link between implantable medical device 101 and, for example, an external assembly 140.

In some instances, implantable medical device 101 can be configured to perform vector assessments. For example, processor circuit 103 can cause electro-stimulation circuit 105 to deliver electrical stimulation via some or all of the vectors created by pairs of electrodes connected to implantable leads 110, 120, and 130. Sensing circuit 106 may detect various parameters during the vector assessment and store the detected parameters in memory circuit 104. In some cases, processor circuit 103 may communicate the detected parameters to external assembly 140, via communication circuit 102.

Implantable medical device 101 can be configured to communicate (wired or wirelessly) via communication circuit 102 with a local or remote external device, such as external assembly 140. This can include using an RF, optical, acoustic, or other communication link. External assembly 140 can be a portion or part of a patient management system. In an example, external assembly 140 can communicate with one or more remote clients, such as web-based clients, or can be communicatively coupled to one or more servers, which can include medical and patient databases.

In some cases, external assembly 140 can include communication circuit 142, processor circuit 143, memory circuit 144, or user interface 145. In one example, communication circuit 142 can include inductive coils or radio frequency telemetry circuitry, and can be configured to communicate with implantable medical device 101. Processor circuit 143 and memory circuit 144 can be used to interpret information received from user interface 145, or can be used to determine when to use communication circuit 142 to exchange information with implantable medical device 101. In one example, processor circuit 143 and memory circuit 144 can be used to initiate a vector assessment controlled at least in part by external assembly 140 using electrode system 107. External assembly 140 can be used to perform vector assessments using electrode system 107 and can be configured to display results such as by using user interface 145. In some cases, the external assembly 140 is not used, and it is the implantable medical device 101 that is configured to perform vector assessments using electrode system 107.

When used, external assembly 140 can be an adjunct (e.g., non-implantable) external assembly. In one example, external assembly 140 can include the features of implantable medical device 101 described above and below, such that external assembly 140 can be configured to be directly or indirectly coupled to the electrode system 107. For example, external assembly 140 can be configured to assess each of the potential vectors resulting from all the various combinations of electrodes 112, 114, 116, 118, 122, 124, 126, 132, and 134. External assembly 140 may be able to perform an assessment by utilizing a power source (not shown) to deliver electrical stimulation pulses to electrode system 107. External assembly 140 may be equipped with one or more algorithms that automatically select one or more of the assessed vectors and configures implantable medical device 101 with the selected vectors. In other examples, a user, such as a physician or other medical professional, may view results of the assessment and provide selections of one or more vectors. These selected vectors may be communicated to implantable medical device 101 via communication circuit 142. By using external assembly 140 to perform vector assessments, implantable medical device 101 may conserve power.

User interface 145 of external assembly 140 can include, but is not limited to, a keyboard, a mouse, a light pen, a touch-screen, a display screen, a printer, or an audio speaker. In one example, user interface 145 can be configured as a full color, high definition graphical display, such as using an LCD computer monitor. In another example, user interface 145 can be configured for use as a monochromatic display, such as using a CRT monitor to display text. In some examples, user interface 145 can be configured to interactively present a graphical representation of vector assessments to a user. In other examples, user interface 145 can be configured to interactively present a text-based representation of vector assessments.

Figure 2:
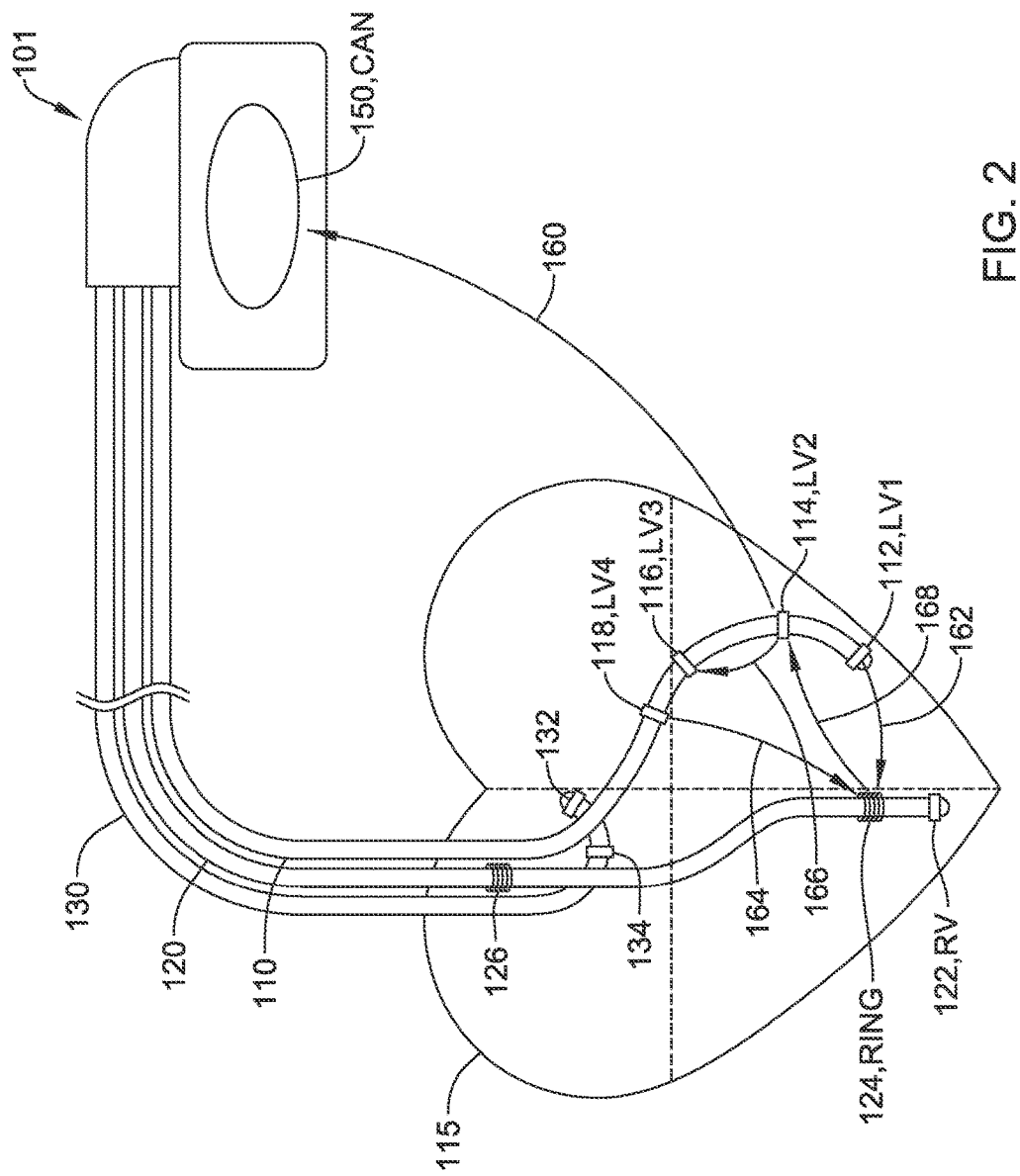
FIG. 2 is a schematic diagram of an implantable medical system including exemplary vectors.

FIG. 2 is a schematic diagram of the implantable medical system of FIG. 1 including exemplary vectors. As described with respect to FIG. 1, each pair of electrodes of implantable medical device 101 may be considered a vector. For each pair of electrodes, a first one of the electrodes is a cathode electrode and a second one of the electrodes is an anode electrode. In each of the illustrated example vectors, the arrow of each vector points to the anode electrode and the base of each arrow points to the cathode electrode. Although each vector is drawn as an arrow indicating a pathway, the vector only represents a general flow of electrical stimulation propagation when electrical stimulation is delivered via the particular vector. The exact pathway of electrical stimulation propagation will depend on many factors including physiological and physical system factors.

In some examples, implantable medical device 101 further includes can electrode 150, as shown in FIG. 2. FIG. 2 further illustrates example vectors 160, 162, 164, 166, and 168. In FIG. 2 electrodes 112, 114, 116, 118, 122, 124, and 150 are also labeled as LV1, LV2, LV3, LV4, RV, RING, and CAN (sometimes referred to in the art as Q), respectively, which are terms sometimes used in the art. Vector 160 represents the pair of the CAN electrode and the LV2 electrode, where the CAN electrode is an anode electrode and the LV2 electrode is a cathode electrode. The other vectors 162, 164, 166, and 168 all represent examples of vectors of implantable medical device 101. It should be understood that any combination of electrodes may represent a unique vector. Additionally, each pair of electrodes can actually produce two vectors because either of the pair of electrodes can be the cathode electrode or the anode electrode. Table 1, below, lists all of the possible vectors of implantable medical device 101 comprising the RV, LV1, LV2, LV3, LV4, and CAN electrodes. The totality of possible vectors of implantable medical device 101 would further comprise combinations including electrodes 126, 132, 134, and RING. However, it should be understood that in other implantable medical device systems, particularly those with differing amounts of electrodes, the number of vectors of the system may be different. The example techniques described herein may be applicable to any such system including multiple electrodes.

TABLE 1

| Vector | Electrode Combination (Cathode Electrode → Anode Electrode) |
|---|---|
| Vector 1 (164) | LV1 → RV |
| Vector 2 | LV1 → LV4 |
| Vector 3 | LV1 → LV3 |
| Vector 4 | LV1 → LV2 |
| Vector 5 | LV1 → CAN |
| Vector 6 (184) | LV2 → RV |
| Vector 7 | LV2 → LV4 |
| Vector 8 | LV2 → LV3 |
| Vector 9 | LV2 → LV1 |
| Vector 10 (160) | LV2 → CAN |
| Vector 11 (182) | LV3 → RV |
| Vector 12 | LV3 → LV4 |
| Vector 13 (166) | LV3 → LV2 |
| Vector 14 | LV3 → LV1 |
| Vector 15 | LV3 → CAN |
| Vector 16 (162) | LV4 → RV |
| Vector 17 | LV4 → LV1 |
| Vector 18 | LV4 → LV2 |
| Vector 19 | LV4 → LV3 |
| Vector 20 | LV4 → CAN |
| Vector 21 | RV → LV1 |
| Vector 22 | RV → LV2 |
| Vector 23 (168) | RV → LV3 |
| Vector 24 | RV → LV4 |
| Vector 25 | RV → CAN |
| Vector 26 | CAN → RV |
| Vector 27 | CAN → LV1 |
| Vector 28 | CAN → LV2 |
| Vector 29 | CAN → LV3 |
| Vector 30 | CAN → LV4 |

As discussed above, in some examples, implantable medical device 101 may deliver CRT via multiple vectors. For example, implantable medical device 101 may be configured to deliver CRT via Vector 6 and via Vector 16. In general, implantable medical device 101 may be configured to deliver CRT via any combination of vectors available for implantable medical device 101. A determination of when to deliver CRT via a single vector ("single-site pacing") or a plurality of vectors ("multi-site pacing"), and which of the plurality of vectors to use in multi-site pacing configurations, is discussed further below.

Figure 3:
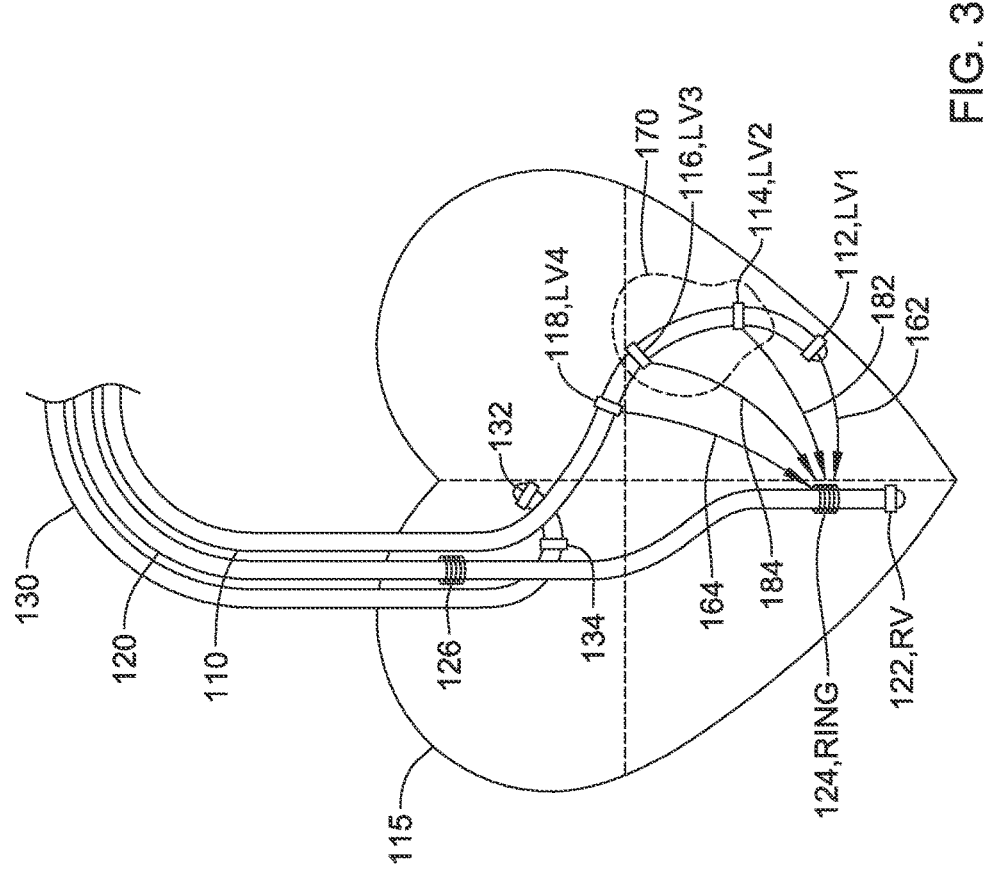
FIG. 3 is a schematic diagram of an implantable medical device system and a heart that has an electrically delayed zone.

FIG. 3 is a schematic diagram of an implantable medical device system, and a heart that includes an electrically delayed zone 170. FIG. 3 also depicts vectors 162, 164, 182, and 184, of which vectors 182 and 184 may originate within or pass through electrically delayed zone 170. Electrically delayed zone 170 may represent diseased cardiac tissue. As described above, such diseased cardiac tissue may not conduct electrical signals or may conduct electrical signals more slowly than the surrounding cardiac tissue. Accordingly, delivering CRT via vectors 182 or 184 may result in a non-synchronous contraction of heart 115. For example, delivering CRT via vector 164 may result in the electrical stimulation propagating throughout the healthy cardiac tissue more quickly relative to electrically delayed zone 170. In such an example, the healthy cardiac tissue, having received the relatively quickly propagating electrical stimulation may contract in a near-synchronous manner. However, the cardiac tissue of electrically delayed zone 170 may contract relatively later than the healthy cardiac tissue, this resulting in a dis-synchronous contraction. Additionally, the cardiac tissue of electrically delayed zone 170 may even contract dis-synchronously with respect to other cardiac tissue in electrically delayed zone 170, as the electrical stimulation propagates more slowly within electrically delayed zone 170. Moreover, and depending on the size and shape of the electrically delayed zone 170, electrical signals that need to travel to regions adjacent the electrically delayed zone 170 may be blocked or need to be re-routed around the electrically delayed zone 170, contributing to delay and dis-synchronous contractions. These dis-synchronous contractions produce a relatively inefficient cardiac contraction, which can be a cause for many different health problems.

Accordingly, in many instances it may be beneficial for implantable medical device 101 to deliver CRT via a vector which originates within or passes through electrically delayed zone 170. For example, if implantable medical device 101 delivers CRT via vector 182 or 184, the CRT may cause the heart to contract in a more synchronous manner than delivering CRT via vectors 162 or 164. In such examples, as the electrical stimulation originates within electrically delayed zone 170, the electrical stimulation may propagate through a portion of electrically delayed zone 170 before reaching the surrounding healthy cardiac tissue. As the electrical stimulation of the CRT propagates throughout electrically delayed zone 170, the diseased cardiac tissue will begin to contract. Once the electrical stimulation propagates through electrically delayed zone 170 to the surrounding healthy cardiac tissue, the electrical stimulation will propagate relatively quickly, thereby causing the healthy cardiac tissue to also contract. This sequence may results in a more synchronous contraction of the heart than delivering CRT via vectors that do not originate within or pass through diseased cardiac tissue, such as electrically delayed zone 170. Moreover, the electrical stimulation that is delivered to the electrically delayed zone 170 may be advanced in time to help compensate for the expected delay in the electrically delayed zone 170.

In some cases, it may be beneficial for implantable medical device 101 to deliver CRT via a plurality of vectors, such as via Vector 182 and Vector 184. In the example shown, both of vectors 182 and 184 reside within electrically delayed zone 170. Accordingly, delivering CRT via both vectors 182 and 184 may increase the rate at which the electrical stimulation propagates through and fully saturates electrically delayed zone 170 and the surrounding regions, as delivering CRT via both vectors 182 and 184 produces two separate locations within electrically delayed zone 170 where the electrical stimulation originates. Alternatively, in some examples, it may be beneficial to deliver CRT via a plurality of vectors where at least one of the vectors (or all of the vectors) do not originate within electrically delayed zone 170, such as via Vector 162 and Vector 184 or Vector 118 and Vector 162.

In examples where implantable medical device 101 is able to deliver CRT via a plurality of vectors, it may be desirable to determine whether it would be beneficial for a patient for implantable medical device 101 to deliver CRT via multiple vectors (e.g. using multi-site pacing), particularly since multi-site pacing often causes extra drain on the battery of implantable medical device 101 relative to single-site pacing. Accordingly, at the time implantable medical device 101 is implanted within a patient, a physician or other medical professional may cause implantable medical device 101 or external assembly 140 to perform an assessment of the vectors of implantable medical device 101. For example, the physician may operate implantable medical device 101, or in some examples, external assembly 140, to perform an assessment of all (or a subset of all) of the potential vectors of implantable medical device 101. Such an assessment may measure many parameters of the vectors such as impedance, phrenic nerve stimulation, signal to noise ratio, capture threshold voltage, and electrical delay to name a few. The impedance, phrenic nerve stimulation, signal to noise ratio, and/or capture threshold voltage of a vector may be used to determine whether that particular vector is viable for delivering CRT. The electrical delay of a vector may be used to determine whether a particular patient would benefit from multi-site pacing, taking into consideration the extra drain on the battery of implantable medical device 101. Accordingly, as part of the assessment of the vectors, implantable medical device 101 may record an electrical delay for each of the viable vectors or electrodes. In general, this electrical delay is a measure of time between delivering electrical stimulation to a cathode electrode and detecting the electrical stimulation at an anode electrode for a given vector (i.e. given pair of electrodes). Differing delay times between vectors can indicate the presence of electrically delayed zones or other conditions of the heart.

As one illustrative example using the vectors illustrated in FIG. 3, a physician may direct implantable medical device 101 or external assembly 140 to perform an assessment of vectors 162, 164, 182, and 184. As an example only, the results of the assessment may produce electrical delay times, such as:

TABLE 2

| Vector | Electrical Delay (ms) |
|---|---|
| 162 | 40 |
| 164 | 45 |
| 182 | 80 |
| 184 | 100 |

Each of these electrical delay times may additionally be associated with specific electrodes. For example, instead of, or in addition to, associating electrical delay with vectors, implantable medical device 101 may associate electrical delay with individual electrodes. In some examples, an electrical delay associated with LV1 may imply an electrical delay between LV1 and RING, where LV1 is a cathode electrode. Continuing the example, implantable medical device 101 or external assembly 140 may indicate that electrical delay times above an electrical delay threshold indicate the presence of an electrically delayed zone, such as electrically delayed zone 170, or other condition that indicates that the patient may benefit from multi-site pacing. Accordingly, implantable medical device 101 or external assembly 140 may recommend configuring implantable medical device 101 to initially deliver CRT via multiple vectors.

In some examples, the electrical delay threshold may be, for example, 70 ms. Accordingly, in this illustrative example, both Vector 182 and Vector 184 have electrical delay times above the electrical delay threshold. In some examples, where more than one vector has an electrical delay above the electrical delay threshold, implantable medical device 101 or external assembly 140 may recommend configuring implantable medical device 101 to deliver CRT via all of the vectors that have electrical delay times greater than the electrical delay threshold, or some subset of the vectors. For example, since Vector 182 and Vector 184 both have electrical delay times greater than 70 ms, implantable medical device 101 or external assembly 140 may recommend configuring implantable medical device 101 to deliver CRT via both Vector 182 and Vector 184.

In some examples, no vectors or only a single vector may have an electrical delay time greater than the electrical delay threshold. In such examples, implantable medical device 101 or external assembly 140 may recommend configuring implantable medical device 101 to deliver CRT via the single vector, such as the vector with the longest delay.

In some instances, implantable medical device 101 or external assembly 140 may take into consideration additional factors in recommending vectors via which to deliver CRT. For example, each electrode may additionally be associated with a position on its lead. As an illustrative example only, in the example of FIG. 3, LV4 may be associated with a position 0, LV3 may be associated with a position 15, LV2 may be associated with a position 30, and LV1 may be associated with a position 45, where each position relates how many millimeters the electrode is away from position 0, following the path of the lead 110. Accordingly, implantable medical device 101 or external assembly 140 may take into consideration a threshold electrode spacing when recommending via which vector or vectors to deliver CRT. For example, if two vectors have electrical delays greater than the electrical delay threshold, but the difference in positions between the cathode electrodes of the two vectors is less than a threshold electrode spacing, implantable medical device 101 or external assembly 140 may recommend configuring implantable medical device 101 to deliver CRT via a single one of the two vectors with electrical delays greater than the electrical delay threshold rather than both. In such examples, implantable medical device 101 or external assembly 140 may recommend configuring implantable medical device 101 to deliver CRT via the vector with the greater electrical delay. In other examples, implantable medical device 101 or external assembly 140 may recommend configuring implantable medical device 101 to deliver CRT via the vector with the lesser electrical delay.

In examples where implantable medical device 101 or external assembly 140 recommend configuring implantable medical device 101 to deliver CRT via a plurality of vectors, implantable medical device 101 or external assembly 140 may further recommend various parameters for delivering CRT. For example, implantable medical device 101 or external assembly 140 may recommend configuring implantable medical device 101 to deliver CRT via a plurality of vectors with a pacing offset. For example, the pacing offset may be a time period between delivering CRT via a first of the recommended vectors and a second of the recommended vectors. In some examples, the pacing offset between the recommended vectors may be the difference in the electrical delay between the vectors. Continuing the example of FIG. 3 above, implantable medical device 101 or external assembly 140 may recommend configuring implantable medical device 101 to deliver CRT via both Vector 182 and Vector 184. Additionally, implantable medical device 101 or external assembly 140 may recommend configuring implantable medical device 101 to deliver CRT via Vector 184 with a pacing offset relative to delivering CRT via Vector 182. Specifically, implantable medical device 101 or external assembly 140 may recommend configuring implantable medical device 101 to deliver CRT via Vector 184 with a pacing offset of 10 ms relative to delivering CRT via Vector 182. In this example, 10 ms is half of the difference between the electrical delay of Vector 182 and Vector 184. In other examples, the recommended pacing offset may be a factor of the difference between the electrical delay of Vector 182 and Vector 184, such as one-quarter, one-third, one-half, two, three, or the like.

Alternatively, implantable medical device 101 or external assembly 140 may not make any recommendations for configuring implantable medical device 101. Instead, implantable medical device 101 or external assembly 140 may automatically configure implantable medical device 101 to deliver CRT via determined vectors according the process described above. In other examples, implantable medical device 101 or external assembly 140 may simply cause the results of the vector assessment to be displayed on a user interface, such as user interface 145. A physician or other medical professional may view the results of the vector assessment. The physician may then make determinations as to which vectors implantable medical device 101 should deliver CRT. The physician may then configure implantable medical device 101 to deliver CRT via the determined vectors. In some examples, the physicians may follow a similar decision process to that described above.

Although the above described process was mainly illustrated with respect to either a single vector or two vectors having electrical delays greater than an electrical delay threshold, this description may be extrapolated to three, or four, or any amount of vectors having an electrical delay greater than a threshold electrical delay. For example, in a situation where three vectors have an electrical delay greater than the electrical delay threshold, implantable medical device 101 or external assembly 140 may recommend configuring implantable medical device 101 to deliver CRT via all three of the vectors. However, in some examples, implantable medical device 101 or external assembly 140 may recommend configuring implantable medical device 101 to deliver CRT via a maximum of two vectors, regardless of the amount of vectors with electrical delays greater than an electrical delay threshold. In such examples, implantable medical device 101 or external assembly 140 may recommend configuring implantable medical device 101 to deliver CRT via the two vectors with the greatest electrical delay. Implantable medical device 101 or external assembly 140 may additionally take into consideration the positions of the cathode electrodes of the vectors relative to each other. If any two cathode electrodes of recommended vectors are positioned less than a threshold electrode spacing away from each other, implantable medical device 101 or external assembly 140 may recommend configuring implantable medical device 101 to deliver CRT via only one of the pair of recommended vectors. In this way, implantable medical device 101 or external assembly 140 can recommend via which vectors to deliver CRT in examples where any number of vectors have electrical delays greater than an electrical delay threshold.

The above description centered on initially configuring implantable medical device 101 via which vectors to deliver CRT at the time of implanting implantable medical device 101 within a patient. However, after initially being configured to deliver CRT via one or more vectors, implantable medical device 101 may periodically perform vector assessments to detect any changes in electrical delays of vectors. For example, as physiological systems, such as the electrical system of a heart, tend to change over time, it is important to periodically reassess whether it would be beneficial to deliver CRT via a single or a plurality of vectors and via which specific vectors. Accordingly, implantable medical device 101 may perform an assessment of the vectors in the manner described above. In some examples, implantable medical device 101 may only perform an assessment on specific vectors stored in memory circuit 104. For example, during the assessment at the time of implantation, implantable medical device 101, external assembly 140, or a physician may store a list of potential vectors within memory circuit 104. These vectors may have been determined based on the other parameters of the assessment such as impedance, phrenic nerve stimulation, LV capture threshold, or signal to noise ratio. In this way, implantable medical device 101 may only perform an assessment on a subset of all of the possible vectors available in implantable medical device 101. Additionally in some examples, implantable medical device 101 may only perform an assessment of the electrical delay times of the stored vectors.

In other examples, implantable medical device 101 is configured to periodically measure the electrical delay of only the vectors via which implantable medical device 101 is configured to deliver CRT. Implantable medical device 101 may additionally store the determined electrical delays for those vectors in memory circuit 104. Implantable medical device 101 may also determine a difference between a newly determined electrical delay for the vector or vectors and one or more stored electrical delays. If the difference between any of these delays is greater than a predetermined threshold, implantable medical device 101 may be configured to perform a full assessment of all potential vectors, as described in any of the sections above. For example, the full assessment may comprise determining an impedance, phrenic nerve stimulation, signal to noise ratio, an LV capture threshold, and an electrical delay for all potential vectors of implantable medical device 101. Alternatively, implantable medical device 101 may only perform such an assessment on those vectors stored in memory circuit 104. In still other examples, the full assessment may comprise only determining new electrical delays for all potential vectors, or only for those vectors stored in memory circuit 104. Based on the results of such an assessment, in accordance with the techniques described above, implantable medical device 101 may be configured, such as by processor circuit 103, to adjust the amount and/or the specific vector or vectors via which implantable medical device 101 delivers CRT.

In some examples, implantable medical device 101 is configured to perform an assessment or determine electrical delays once a day. In other examples, implantable medical device 101 is configured to perform an assessment or determine electrical delays once a week, once a month, once every two months, or once in any particular time period. In still other examples, implantable medical device 101 may be configured to perform an assessment or determine electrical delays periodically, except when an input from an external sensor is above a threshold. For example, physical activity may result in an increased heart rate and perfusion of the heart. This increase heart rate or blood flow may temporarily alter the electrical delay of the vectors. Accordingly, it may be detrimental to perform an assessment or determine electrical delays during times of increased physical activity and to change the determination of which vector or vectors to deliver CRT. In such examples, implantable medical device 101 may be further configured to receive activity level information from an activity sensor, such as via communication circuit 102. When a period comes for implantable medical device 101 to perform an assessment or determine electrical delays, implantable medical device 101 may compare the activity level information from the activity sensor against an activity threshold. If the activity level is above the activity threshold, implantable medical device 101 may delay the assessment or determining of electrical delays. For example, implantable medical device 101 may skip the assessment for the current time period and simply wait until the next time period occurs. In other examples, implantable medical device 101 may delay the assessment or determining of electrical delays for a period of time, such as a number of minutes or hours. After the delay period has passed, implantable medical device 101 may receive new activity level information from the activity sensor and compare the new activity level against the activity level threshold. Implantable medical device 101 may continue this cycle until a period occurs where the activity level is less than or equal to the activity level. Implantable medical device 101 may then perform the assessment or determine electrical delays. In other examples, implantable medical device 101 may be configured to perform an assessment or determine electrical delays at a specific time of day wherein the probability of the heart being in a normal, resting state is high, such as during nighttime or early morning hours.

Alternatively, in some instances, an assessment may be triggered by detecting an increase and/or decrease in activity of the patient. For example, in some instances, the physiology of a patient may be such that it is desirable to perform multi-site pacing when the patient is active and single-site pacing when the patient in inactive, or visa-versa. Performing an assessment in each of the activity states may identify an appropriate vector/vectors for each activity state. Thereafter, when an activity state is detected, the implantable medical device 101 may use the appropriate vector/vectors for the detected state as determined during the assessment.

Moreover, in some instances, the electrical delay threshold may be changed over time. For example, it is contemplated that the electrical delay threshold may be changed based on patient activity, heart rate, sleep status, length of time since implant of the implantable medical device 101, and/or any other suitable parameter or parameters.

Based on the results of any of the above describes assessments or determining electrical delays, implantable medical device 101 may adjust the number of vectors, and which specific vectors, via which implantable medical device 101 delivers CRT. In this manner, implantable medical device 101 is able to adjust between single and multi-site pacing, only employing multi-site pacing when the results of the assessments or determined electrical delays indicates that a patient may benefit from such multi-site pacing. By adjusting vectors in this manner, implantable medical device 101 may operate to conserve battery life. Additionally, by having the ability to perform multi-site pacing, implantable medical device 101 may in some cases produce a more synchronous, and therefore, more efficient contraction of the heart.

In still other examples, after adjusting which vectors implantable medical device 101 delivers CRT, implantable medical device 101 may confirm that the change has resulted in better contractility of the heart. For example, implantable medical device 101 may be configured to receive information from one or more sensors. In examples where the sensors are external to implantable medical device 101, implantable medical device 101 may receive information from the sensors via communication circuit 102. Some example sensors include heart sound sensors, blood pressure sensors, and accelerometers. Implantable medical device 101 may receive new information from one or more such sensors after adjusting via which vectors implantable medical device 101 delivers CRT. Implantable medical device 101 may then compare the new information with information from the one or more sensors stored in memory circuit 104. Based on the comparison of the information, implantable medical device 101 may determine whether the adjustment of the vectors has increased the contractility of the heart. For example, implantable medical device 101 may receive blood pressure information from a blood pressure sensor after adjusting the vectors via which implantable medical device 101 delivers CRT that indicates increased heart rate or left ventricular blood pressure relative to the heart rate or left ventricular blood pressure information stored in memory circuit 104 from before implantable medical device 101 made the adjustment of the vectors. In such examples, implantable medical device 101 may determine that the adjustment of the vectors has increased contractility of the heart. Similar determinations may be made for other types of information, such as the strength of the signal from any heart sounds sensors or the strength of the signal from accelerometers. In examples where implantable medical device 101 switched from single-site pacing to multi-site pacing, but has determined based on information from the additional sensors that the adjustment did not increase the contractility of the heart or other mechanical function of the heart as indicated by the sensors, implantable medical device 101 may switch back to single-site pacing. In such examples where switching from single-site pacing to multi-site pacing does not appear to increase the contractility of the heart or other mechanical function of the heart, it may be beneficial to continue on with single-site pacing, as single-site pacing uses relatively less energy.

Figure 4:
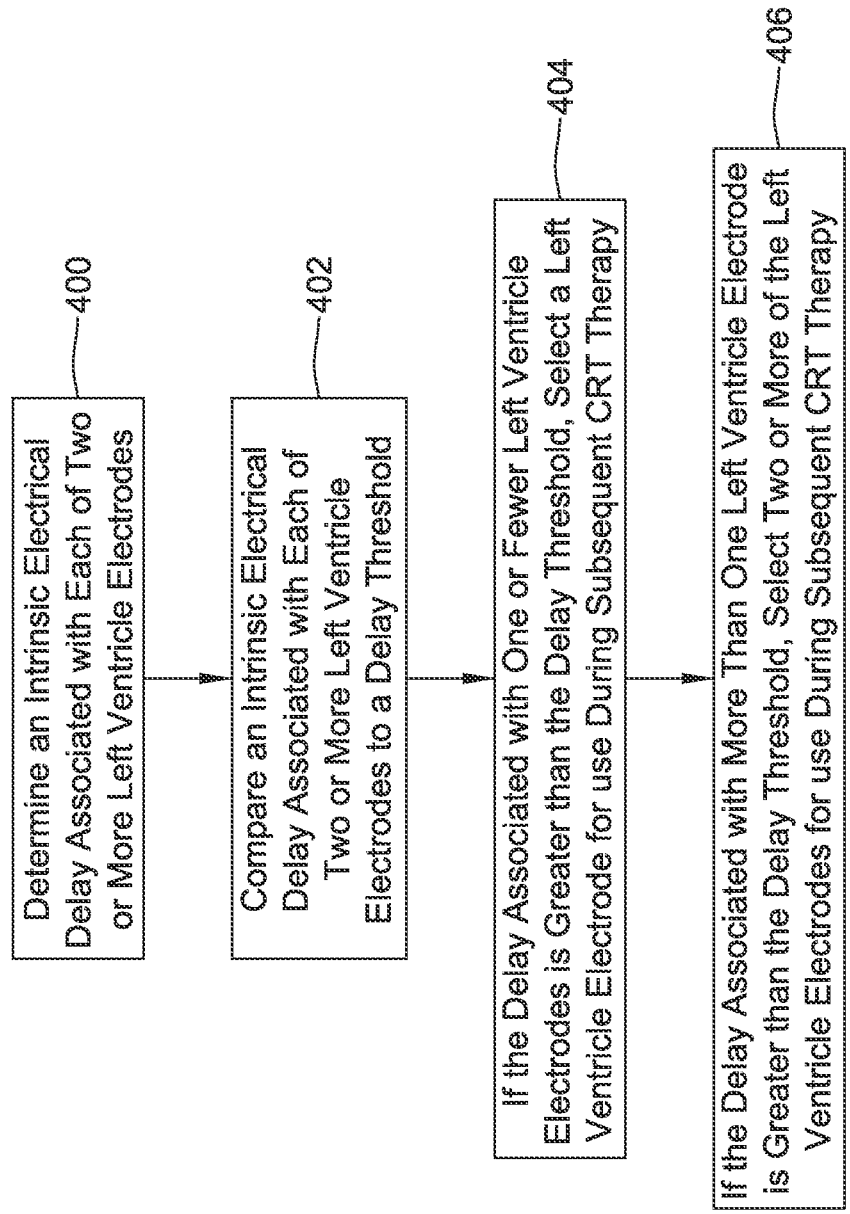
FIG. 4 is a flow diagram of a method that may be implemented by an implantable medical device system such as shown in FIG. 1.

FIG. 4 is a flow diagram of a method that may be implemented by an implantable medical device system such as shown in FIG. 1. Although the method of FIG. 4 will be described with respect to the medical device system of FIG. 1, the method of FIG. 4 may be performed by any suitable medical device system.

A medical device system, such as system 100 of FIG. 1, may determine an electrical delay between two or more left ventricle electrodes (400). For example, implantable medical device 101 may deliver electrical stimulation pulses to one or more cathode electrodes and sense for the delivered electrical stimulation pulses at one or more anode electrodes. In one example, implantable medical device 101 may deliver one or more electrical stimulation pulses via RV electrode in the right ventricle of heart 115. Implantable medical device 101 may additionally sense for the delivered electrical stimulation pulse or pulses at one or more of LV1-LV4 electrodes in the left ventricle of heart 115. The determined electrical delay between delivering the electrical stimulation to the cathode electrode and detecting the electrical stimulation at the anode electrode may be termed a paced electrical delay. In other examples, the electrical delay may comprise an intrinsic electrical delay. For example, implantable medical device 101 may sense an intrinsic depolarization wave with one or more electrodes in the right ventricle of heart 115, such as RV electrode. Implantable medical device 101 may additionally sense the intrinsic depolarization wave with one or more electrodes in the left ventricle of heart 115, such as any of LV1-LV4 electrodes. The determined difference in time between sensing with an electrode in the right ventricle and sensing with an electrode in the left ventricle may be the intrinsic electrical delay associated with a left ventricle electrode. In still other examples, implantable medical device may determine an electrical delay (either paced or intrinsic) associated with any combination of electrodes. Implantable medical device 101 may then compare the determined electrical delays to an electrical delay threshold (402).

If the electrical delay associated with one or fewer left ventricle electrodes is greater than the electrical delay threshold, implantable medical device 101 may select a left ventricle electrode for use during subsequent CRT therapy (404). For example, after determining only a single electrical delay associated with a left ventricle electrode is greater than the electrical delay threshold, implantable medical device 101 may be configured, such as by processor circuit 103, to deliver CRT therapy via that particular left ventricle electrode. If the delay associated with more than one left ventricle electrode is greater than the delay threshold, implantable medical device 101 may select two or more of the left ventricle electrodes for use during subsequent CRT therapy (406). For example, after determining that more than one electrical delay associated with left ventricle electrodes are greater than the electrical delay threshold, implantable medical device 101 may be configured, such as by processor circuit 103, to deliver CRT therapy via a plurality of left ventricle electrodes.

Figure 5:
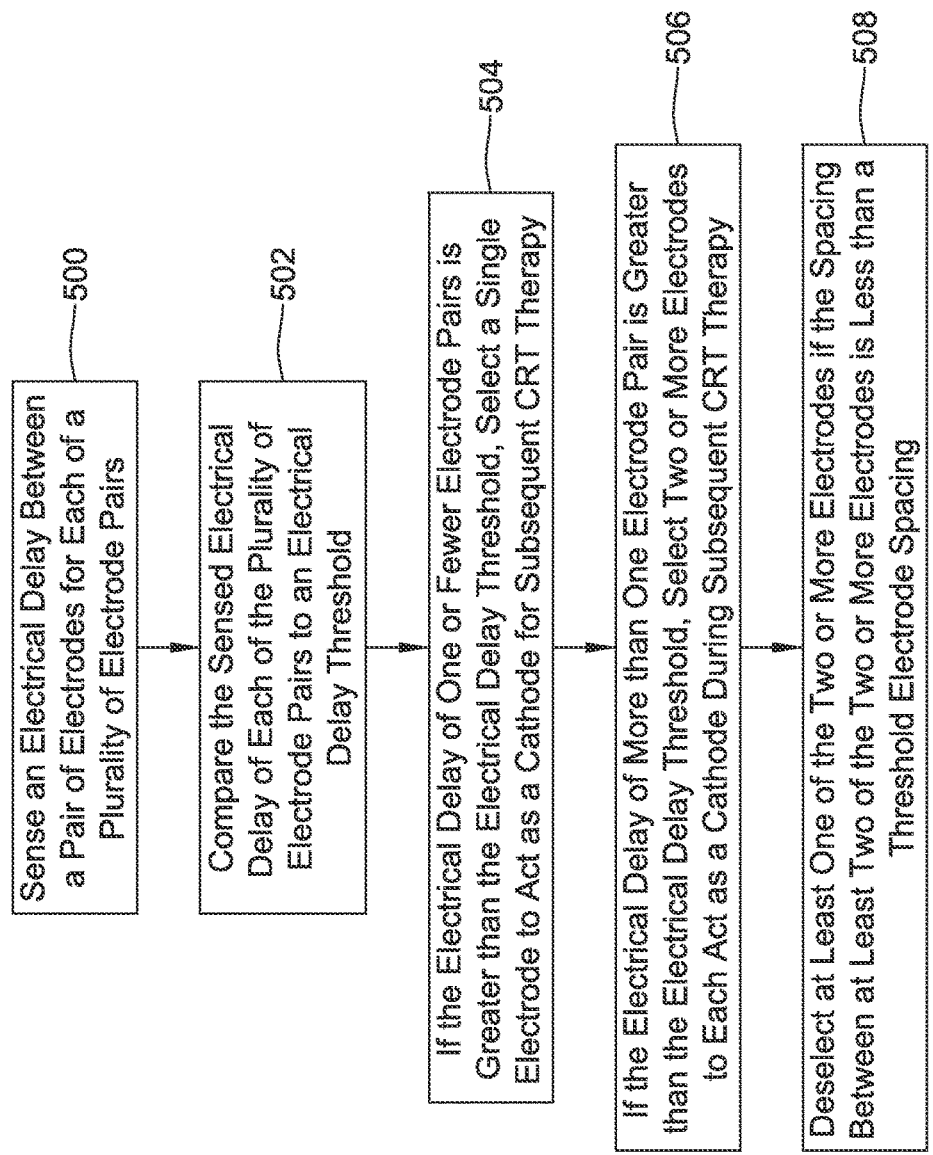
FIG. 5 is a flow diagram of a method that may be implemented by an implantable medical device system such as shown in FIG. 1.

FIG. 5 is a flow diagram of a method that may be implemented by an implantable medical device system such as shown in FIG. 1. Although the method of FIG. 4 will be described with respect to the medical device system of FIG. 1, the method of FIG. 4 may be performed by any suitable medical device system.

A medical device system, such as system 100 of FIG. 1, may determine an electrical delay between a pair of electrodes for each of a plurality of electrode pairs (500). For example, implantable medical device 101 may deliver electrical stimulation pulses to a cathode electrode, for example RV electrode, in the right ventricle of heart 115. Implantable medical device 101 may further sense the delivered electrical stimulation at an anode electrode in heart 115, for example any of LV1-LV4 electrodes. The delay between delivering the electrical stimulation to the cathode electrode and sensing the electrical stimulation at the anode electrode is the determined paced electrical delay. Implantable medical device 101 may further deliver and sense electrical stimulation for each pair of a cathode electrode and an anode electrode. In other examples, implantable medical device 101 may determine an intrinsic electrical delay by sensing a depolarization wave with a first electrode and sensing the same depolarization with a second electrode. The difference in time between sensing the depolarization wave with the first electrode and sensing the wave with the second electrode may be the intrinsic electrical delay. In any case, implantable medical device 101 may determine an electrical delay between any combination of electrodes. Implantable medical device 101 may then compare the sensed electrical delay of each of the plurality of electrode pairs to an electrical delay threshold (502).

If the electrical delay of one or fewer electrode pairs is greater than the electrical delay threshold, implantable medical device 101 may select a single electrode to act as a cathode for subsequent CRT therapy (504). For example, after determining only a single electrical delay is greater than the electrical delay threshold, implantable medical device 101 may be configured, such as by processor circuit 103, to deliver CRT therapy via that particular electrode, where that electrode acts as a cathode electrode. If the electrical delay of more than one electrode pair is greater than the electrical delay threshold, implantable medical device 101 may select two or more electrodes to each act as a cathode during subsequent CRT therapy (506). For example, after determining that more than one electrical delay is greater than the electrical delay threshold, implantable medical device 101 may be configured, such as by processor circuit 103, to deliver CRT therapy via a plurality of electrodes, where each of the plurality of electrodes acts as a cathode electrode. Implantable medical device 101 may be further configured to deselect at least one of the two or more electrodes if a spacing between at least two of the two or more electrodes is less than a threshold electrode spacing (508). For example, each electrode may be associated with a position on the lead carrying the electrode. In such examples, if, based on the comparison of electrical delays, implantable medical device 101 selects two or more electrodes to act as cathode electrodes for delivering CRT therapy, implantable medical device 101 may additionally deselect at least one of the two or more electrodes if the difference between the positions associated with two or more of the selected electrodes is less than a threshold.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method of providing CRT therapy to a patient with an implanted multi-site pacing medical device, wherein the method comprises:
    determining an electrical delay associated with each of two or more left ventricle electrodes;
    comparing the electrical delay associated with each of the two or more left ventricle electrodes to an electrical delay threshold;
    if the electrical delay associated with one or fewer left ventricle electrodes is greater than the electrical delay threshold, selecting a first number of left ventricle electrodes for use during subsequent CRT therapy; and
    if the electrical delay associated with more than one left ventricle electrode is greater than the electrical delay threshold, selecting a second number of the left ventricle electrodes for use during subsequent CRT therapy, wherein the second number of the electrodes is greater than the first number of electrode.

2. The method of claim 1, wherein:
    if the electrical delay associated with one or fewer left ventricle electrodes is greater than the electrical delay threshold, selecting the one left ventricle electrode with the longest associated electrical delay for use during subsequent CRT therapy.

3. The method of claim 1, wherein:
    if the electrical delay associated with more than one left ventricle electrode is greater than the electrical delay threshold, selecting two or more of the left ventricle electrodes that have associated electrical delays that are greater than the electrical delay threshold for use during subsequent CRT therapy.

4. The method of claim 3, wherein the two or more of the left ventricle electrodes that are selected for use during subsequent CRT therapy are each paced as cathodes during subsequent CRT therapy.

5. The method of claim 3, wherein at least one of the two or more of the left ventricle electrodes that are selected for use during subsequent CRT therapy is paced as an anode and at least one of the two or more of the left ventricle electrodes is paced as a cathode.

6. The method of claim 1, wherein:
    if the electrical delay associated with more than one left ventricle electrode is greater than the electrical delay threshold, providing a pacing offset between pacing pulses of at least two of the two or more left ventricle electrodes during subsequent CRT therapy.

7. The method of claim 6, wherein the pacing offset between pacing pulses of at least two of the two or more left ventricle electrodes is related to the difference of electrical delays between the at least two of the two or more electrodes.

8. The method of claim 1, wherein the method is initiated at a predetermined interval.

9. The method of claim 1, wherein the method is initiated by a trigger.

10. The method of claim 9, further comprising issuing the trigger when the electrical delay associated with at least one of the two or more left ventricle electrodes changes by more than a predetermined amount.

11. The method of claim 9, wherein the trigger is dependent upon an activity level of the patient.

12. The method of claim 1, wherein the electrical delay associated with each of the two or more left ventricle electrodes corresponds to a QLV delay.

13. The method of claim 1, wherein the electrical delay associated with each of the two or more left ventricle electrodes corresponds to a RV-LV delay.

14. The method of claim 1, further comprising:
    evaluating a physical spacing between the selected two or more of the left ventricle electrodes, and if two or more of the selected electrodes are within a threshold electrode spacing of each other, deselecting all but one of those electrodes for use during subsequent CRT therapy.

15. A method of providing CRT therapy to a patient with an implanted multi-site pacing medical device, wherein the method comprises:
    sensing an electrical delay between a pair of electrodes for each of a plurality of electrode pairs;
    comparing the sensed electrical delay of each of the plurality of electrode pairs to an electrical delay threshold;
    if the sensed electrical delay of one or fewer electrode pairs is greater than the electrical delay threshold, selecting a single electrode to act as a cathode for subsequent CRT therapy; and
    if the sensed electrical delay of more than one electrode pair is greater than the electrical delay threshold, selecting two or more electrodes to each act as a cathode during subsequent CRT therapy.

16. The method of claim 15, wherein selecting two or more electrodes to each act as a cathode further comprises deselecting at least one of the two or more electrodes if a spacing between at least two of the two or more electrodes is less than a threshold electrode spacing.

17. A medical device system for providing CRT therapy to a patient, comprising:
    a pulse generator;
    two or more left ventricle electrodes operatively coupled to the pulse generator;
    a controller, wherein the controller is configured to:
        determine an electrical delay associated with each of the two or more left ventricle electrodes;
        compare the electrical delay associated with each of the two or more left ventricle electrodes to an electrical delay threshold;
        if the electrical delay associated with one or fewer left ventricle electrodes is greater than the electrical delay threshold, selecting a first number of left ventricle electrodes for use during subsequent CRT therapy; and
        if the electrical delay associated with more than one left ventricle electrode is greater than the electrical delay threshold, selecting a second number of the left ventricle electrodes for use during subsequent CRT therapy, wherein the second number is greater than the first number.

18. The medical device system of claim 17, wherein:
    if the electrical delay associated with one or fewer left ventricle electrodes is greater than the electrical delay threshold, the controller selects the one left ventricle electrode with the longest associated delay for use during subsequent CRT therapy.

19. The medical device system of claim 17, wherein:
if the electrical delay associated with more than one left ventricle electrode is greater than the electrical delay threshold, the controller selects two or more of the left ventricle electrodes that have associated electrical delays that are greater than the electrical delay threshold for use during subsequent CRT therapy.

20. The medical device system of claim 17, wherein:
if the electrical delay associated with more than one left ventricle electrode is greater than the electrical delay threshold, the controller providing a pacing offset between pacing pulses of at least two of the two or more left ventricle electrodes during subsequent CRT therapy.

* * * * *